US006402731B1

(12) United States Patent
Suprise et al.

(10) Patent No.: US 6,402,731 B1
(45) Date of Patent: *Jun. 11, 2002

(54) MULTI-FUNCTIONAL FASTENER FOR DISPOSABLE ABSORBENT ARTICLES

(75) Inventors: Jody Dorothy Suprise, Pine River; Paul John Serbiak, Appleton; Timothy James Blenke, Neenah, all of WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/907,585

(22) Filed: Aug. 8, 1997

(51) Int. Cl.[7] ................................................. A61F 13/15
(52) U.S. Cl. ......................... 604/391; 664/392; 664/394
(58) Field of Search ........................... 604/385.1, 385.2, 604/386, 389, 390, 391, 392–396

(56) References Cited

U.S. PATENT DOCUMENTS

| 1,079,479 A | 11/1913 | Earnshaw |
| 1,485,001 A | 2/1924 | Wills |

(List continued on next page.)

FOREIGN PATENT DOCUMENTS

| AU | 667899 | 4/1996 |
| CA | 2096672 | 11/1993 |
| CA | 2103992 | 2/1994 |
| CA | 2187021 | 10/1995 |
| CA | 2187366 | 10/1995 |
| EP | 0 206 208 B1 | 12/1986 |
| EP | 0 217 032 | 4/1987 |

(List continued on next page.)

OTHER PUBLICATIONS

Derwent World Patent Database abstract of FR 2762507 A1: Description of Rahala, "Baby's Disposable Nappy.".
Derwent World Patent Database abstract of JP 6–063076 A: Description of Kao Corp. (Kaos), "Throw Away Diaper or Nappy.".
Derwent World Patent Database abstract of JP 95–044941 B2: Description of Zuiko KK (ZUIK–N), "Simple Solid Diaper for Eliminating Waste of Material by Using Square Shape.".
Derwent World Patent Database abstract of JP 9–276334 A: Description of Kao Corp (Kaos), "Disposable Baby Nappy.".
Derwent World Patent Database abstract of JP 11–070143 A: Description of Toyo Eisai KK (TOEI–N), "Disposable Diaper for Adults and Children.".
Derwent World Patent Database abstract of JP 11–076299 A: Description of Uni–Charm KK (UNIC–N), "Disposable Diaper.".

Primary Examiner—Aaron J. Lewis
Assistant Examiner—K. M. Reichle
(74) Attorney, Agent, or Firm—Jeffery B Curtin

(57) ABSTRACT

A disposable absorbent article includes a multi-functional fastening system which includes a pair of primary fasteners which are located on the opposed side edges in one of the waist regions of the absorbent article. The primary fasteners are configured to releasably engage the opposite waist region of the absorbent article. The fastening system also includes at least one secondary fastener which is located in one of the waist regions of the absorbent article. The secondary fastener is configured to releasably engage the opposite waist region of the absorbent article to conform the waist regions of the article to a wearer's body after the primary fasteners have been releasably engaged. The primary fasteners may be prefastened to allow the disposable absorbent article to be pulled on or off over the wearer's hips. The fastening system may further include a belt segment to which the secondary fasteners are attached.

14 Claims, 6 Drawing Sheets

U.S. PATENT DOCUMENTS

| | | | |
|---|---|---|---|
| 1,657,907 A | * 1/1928 | Abramouich | 604/392 |
| 1,705,194 A | 3/1929 | Marinsky | |
| 1,762,468 A | 6/1930 | Brewer | |
| 1,963,334 A | 6/1934 | Neilson | 2/237 |
| 2,201,255 A | * 5/1940 | Wilson, Jr. | 604/394 |
| 2,242,977 A | * 5/1941 | Marcos | 604/392 |
| 2,475,175 A | 7/1949 | Cadous | 2/237 |
| 2,477,914 A | 8/1949 | Webb | |
| 2,545,761 A | 3/1951 | Brink | |
| 2,570,963 A | 10/1951 | Mesmer | |
| 2,630,120 A | 3/1953 | Nielson | |
| 2,630,806 A | 3/1953 | Kiscaden | |
| 2,743,725 A | 5/1956 | Matthews | |
| 2,801,632 A | 8/1957 | Burner et al. | |
| 2,808,831 A | 10/1957 | Winslett | |
| 2,830,589 A | 4/1958 | Doner | |
| 2,833,282 A | 5/1958 | Moore | |
| 2,910,982 A | 11/1959 | Woodward | |
| 2,931,361 A | 4/1960 | Sostrin | |
| 3,039,466 A | 6/1962 | Wilson | |
| 3,077,193 A | 2/1963 | Mann | |
| 3,610,244 A | 10/1971 | Jones, Sr. | |
| 3,638,651 A | * 2/1972 | Torr | 604/396 |
| 3,653,381 A | 4/1972 | Warnken | |
| 3,825,006 A | 7/1974 | Ralph | |
| 3,882,871 A | 5/1975 | Taniguchi | |
| 4,024,867 A | * 5/1977 | Mesek | 604/396 |
| 4,051,853 A | 10/1977 | Egan, Jr. | |
| 4,051,854 A | 10/1977 | Aaron | |
| 4,066,081 A | 1/1978 | Schaar | |
| 4,074,716 A | 2/1978 | Schaar | |
| 4,089,068 A | 5/1978 | Swallow | 2/76 |
| 4,090,516 A | 5/1978 | Schaar | |
| 4,205,679 A | 6/1980 | Repke et al. | |
| 4,210,143 A | * 7/1980 | De Junckheene | 604/392 |
| 4,315,508 A | 2/1982 | Bolick | 604/392 |
| 4,337,771 A | 7/1982 | Pieniak et al. | |
| 4,409,049 A | 10/1983 | Passafiume et al. | |
| 4,410,327 A | * 10/1983 | Buggaley | 604/391 |
| 4,500,316 A | 2/1985 | Damico | 604/389 |
| 4,515,595 A | 5/1985 | Kievit et al. | |
| 4,522,853 A | 6/1985 | Szonn et al. | 428/40 |
| 4,525,407 A | 6/1985 | Ness | 428/138 |
| 4,563,185 A | 1/1986 | Reiter | |
| 4,568,341 A | 2/1986 | Mitchell et al. | 604/368 |
| 4,581,772 A | 4/1986 | Smith | 2/111 |
| 4,596,055 A | 6/1986 | Aach et al. | 2/237 |
| 4,598,528 A | * 7/1986 | McFarland et al. | 604/385.1 |
| 4,604,096 A | * 8/1986 | Dean et al. | 604/385.2 |
| 4,610,680 A | 9/1986 | LaFleur | |
| 4,610,681 A | 9/1986 | Strohbeen et al. | 604/396 |
| 4,615,695 A | 10/1986 | Cooper | |
| 4,617,022 A | 10/1986 | Pigneul et al. | 604/391 |
| 4,619,649 A | 10/1986 | Roberts | 604/396 |
| 4,623,339 A | 11/1986 | Ciraldo et al. | 604/359 |
| 4,630,320 A | 12/1986 | Van Gompel | 2/406 |
| 4,663,220 A | 5/1987 | Wisneski et al. | 428/221 |
| 4,675,918 A | 6/1987 | O'Brien | 2/402 |
| D290,780 S | 7/1987 | Wistrand | D2/10 |
| 4,699,622 A | * 10/1987 | Toussant et al. | 604/389 |
| 4,704,116 A | 11/1987 | Enloe | |
| 4,726,874 A | 2/1988 | Van Vliet | 156/495 |
| 4,728,326 A | 3/1988 | Gilles | 604/391 |
| 4,743,239 A | 5/1988 | Cole | |
| 4,747,846 A | 5/1988 | Boland et al. | |
| 4,753,646 A | 6/1988 | Enloe | |
| 4,753,650 A | 6/1988 | Williams | 604/389 |
| 4,798,603 A | 1/1989 | Meyer et al. | 604/378 |
| 4,801,485 A | 1/1989 | Sallee et al. | 428/198 |
| 4,808,252 A | 2/1989 | Lash | 156/73.1 |
| 4,826,499 A | 5/1989 | Ahr | 604/389 |
| 4,850,988 A | 7/1989 | Aledo et al. | |
| 4,850,992 A | 7/1989 | Amaral et al. | 604/389 |
| 4,857,067 A | 8/1989 | Wood et al. | 604/389 |
| 4,883,481 A | 11/1989 | Blanchard | |
| 4,892,590 A | * 1/1990 | Stevens et al. | 604/385.1 |
| 4,895,569 A | 1/1990 | Wilson et al. | |
| 4,904,252 A | 2/1990 | Fitzgerald | |
| 4,908,247 A | 3/1990 | Baird et al. | |
| 4,909,802 A | 3/1990 | Ahr et al. | |
| 4,911,702 A | 3/1990 | O'Leary et al. | 604/389 |
| 4,917,682 A | 4/1990 | Lancaster et al. | 604/385.2 |
| 4,936,846 A | * 6/1990 | Proxmine | 604/385.2 |
| 4,937,857 A | * 6/1990 | Schreine | 604/385.1 |
| 4,938,753 A | 7/1990 | Van Gompel et al. | |
| 4,944,733 A | 7/1990 | Casale | |
| 4,961,736 A | 10/1990 | McCloud | |
| 4,964,860 A | 10/1990 | Gipson et al. | 604/391 |
| 4,973,326 A | 11/1990 | Wood et al. | |
| 4,988,346 A | 1/1991 | Pfefferkorn | 604/389 |
| 4,998,929 A | 3/1991 | Bjorksund et al. | 604/385.2 |
| 5,019,072 A | 5/1991 | Polski | 604/389 |
| 5,019,073 A | 5/1991 | Roessler et al. | 604/391 |
| 5,040,244 A | 8/1991 | Tubbs | 2/237 |
| 5,062,839 A | 11/1991 | Anderson | |
| 5,066,289 A | 11/1991 | Polski | 604/389 |
| 5,069,678 A | 12/1991 | Yamamoto et al. | |
| 5,074,854 A | 12/1991 | Davis | |
| 5,087,253 A | 2/1992 | Cooper | |
| 5,106,382 A | 4/1992 | Henry | |
| 5,106,385 A | 4/1992 | Allen et al. | 604/391 |
| 5,110,403 A | 5/1992 | Ehlert | 156/580.1 |
| 5,112,326 A | 5/1992 | Quadrini | 604/391 |
| 5,135,522 A | 8/1992 | Fahrenkrug et al. | |
| 5,140,757 A | 8/1992 | Terada | 34/66 |
| 5,163,932 A | 11/1992 | Nomura et al. | |
| 5,170,505 A | 12/1992 | Rohrer | 2/69 |
| 5,176,668 A | 1/1993 | Bernardin | 604/368 |
| 5,176,670 A | 1/1993 | Roessler et al. | 604/391 |
| 5,176,672 A | 1/1993 | Bruemmer et al. | |
| 5,185,011 A | 2/1993 | Strasser | |
| 5,186,779 A | 2/1993 | Tubbs | 156/161 |
| 5,187,817 A | 2/1993 | Zolner | 2/400 |
| 5,192,606 A | 3/1993 | Proxmire et al. | 428/284 |
| 5,226,992 A | 7/1993 | Morman | 156/62.4 |
| 5,236,430 A | 8/1993 | Bridges | |
| 5,242,436 A | 9/1993 | Weil et al. | |
| 5,246,433 A | 9/1993 | Hasse et al. | |
| 5,275,590 A | 1/1994 | Huffman et al. | |
| 5,300,057 A | 4/1994 | Miller et al. | |
| 5,304,162 A | 4/1994 | Kuen | 604/391 |
| 5,312,387 A | 5/1994 | Rossini et al. | |
| 5,340,431 A | 8/1994 | Terada | 156/359 |
| 5,358,500 A | 10/1994 | Lavon et al. | |
| 5,368,584 A | 11/1994 | Clear et al. | |
| 5,368,585 A | 11/1994 | Dokken | 604/393 |
| 5,370,632 A | 12/1994 | Beplate | |
| 5,370,634 A | 12/1994 | Ando et al. | |
| 5,373,587 A | 12/1994 | Sexton | 2/237 |
| 5,374,262 A | 12/1994 | Keuhn, Jr. et al. | 604/391 |
| 5,383,872 A | 1/1995 | Roessler et al. | 604/391 |
| 5,386,595 A | 2/1995 | Kuen et al. | 2/400 |
| 5,397,639 A | 3/1995 | Tollini | 428/343 |
| 5,399,219 A | 3/1995 | Roessler et al. | 156/259 |
| 5,401,275 A | * 3/1995 | Flug et al. | 604/391 |
| 5,423,789 A | 6/1995 | Kuen | 604/386 |
| 5,445,628 A | 8/1995 | Gipson et al. | 604/392 |
| 5,451,219 A | 9/1995 | Suzuki et al. | |
| 5,462,541 A | 10/1995 | Bruemmer et al. | 604/391 |
| 5,489,282 A | 2/1996 | Zehner et al. | |
| 5,496,298 A | 3/1996 | Kuepper et al. | |

| | | | |
|---|---|---|---|
| 5,499,978 A | 3/1996 | Buell et al. | |
| 5,500,063 A | 3/1996 | Jessup | 156/85 |
| 5,509,915 A | 4/1996 | Hanson et al. | 604/378 |
| 5,527,302 A | 6/1996 | Endres et al. | |
| H1558 H | 7/1996 | Goulait et al. | 156/210 |
| 5,531,731 A | 7/1996 | Brusky | 604/390 |
| 5,531,732 A | 7/1996 | Wood | 604/391 |
| 5,537,722 A | 7/1996 | Niederhofer et al. | 24/304 |
| 5,540,796 A | 7/1996 | Fries | 156/164 |
| 5,545,158 A | 8/1996 | Jessup | |
| 5,545,275 A | 8/1996 | Herrin et al. | 156/731 |
| 5,554,146 A | 9/1996 | Niederhofer et al. | 604/391 |
| 5,562,650 A | 10/1996 | Everett et al. | 604/378 |
| 5,569,232 A | 10/1996 | Roe et al. | |
| 5,569,234 A | 10/1996 | Buell et al. | |
| 5,571,586 A | 11/1996 | Gobran | 428/41.3 |
| 5,575,784 A | 11/1996 | Ames-Ooten et al. | |
| 5,582,606 A | 12/1996 | Bruemmer et al. | |
| 5,591,152 A | 1/1997 | Buell et al. | 604/385.2 |
| 5,593,401 A | 1/1997 | Sosalla et al. | |
| 5,601,546 A | 2/1997 | Tanji et al. | |
| 5,607,416 A | 3/1997 | Yamamoto et al. | 604/397 |
| 5,611,789 A | 3/1997 | Seth | 604/391 |
| 5,618,366 A | 4/1997 | Suekane | 156/73.1 |
| 5,624,420 A | 4/1997 | Bridges et al. | 604/365 |
| 5,624,424 A | 4/1997 | Saisaka et al. | |
| 5,624,428 A | 4/1997 | Sauer | 604/391 |
| 5,624,429 A | 4/1997 | Long et al. | 604/391 |
| 5,626,574 A | 5/1997 | Sasaki et al. | |
| 5,628,738 A | 5/1997 | Suekane | |
| 5,629,063 A | 5/1997 | Gobran | 428/40.1 |
| 5,634,916 A | 6/1997 | Lavon et al. | |
| H1674 H | 8/1997 | Ames et al. | 604/389 |
| 5,656,111 A | 8/1997 | Dilnik et al. | 156/66 |
| 5,662,637 A | 9/1997 | Kitaoka et al. | |
| 5,662,638 A | 9/1997 | Johnson et al. | 604/386 |
| 5,665,084 A | 9/1997 | Richmond | 604/389 |
| 5,669,897 A | 9/1997 | Lavon et al. | |
| 5,685,873 A | 11/1997 | Bruemmer | |
| 5,685,874 A | 11/1997 | Buell et al. | 604/396 |
| 5,690,626 A | 11/1997 | Suzuki et al. | |
| 5,690,627 A | 11/1997 | Clear et al. | |
| 5,693,038 A | 12/1997 | Suzuki et al. | |
| 5,695,488 A | 12/1997 | Sosalla | |
| 5,695,868 A | 12/1997 | McCormack | |
| D389,320 S | 1/1998 | Vinnage et al. | D5/63 |
| 5,707,364 A | 1/1998 | Coates | 604/391 |
| 5,711,832 A | 1/1998 | Glaug et al. | 156/73.1 |
| 5,725,518 A | 3/1998 | Coates | |
| 5,759,317 A | 6/1998 | Justmann | 156/66 |
| 5,772,825 A | 6/1998 | Schmitz | 156/164 |
| 5,788,685 A | 8/1998 | Ronnberg et al. | |
| 5,788,797 A | 8/1998 | Herrin et al. | 156/73.1 |
| 5,795,433 A | 8/1998 | Niedermeyer | |
| 5,827,259 A | 10/1998 | Laux et al. | |
| 5,827,260 A | 10/1998 | Suzuki et al. | |
| 5,830,206 A | 11/1998 | Larsson | 604/390 |
| 5,843,056 A | 12/1998 | Good et al. | |
| 5,855,574 A | 1/1999 | Kling et al. | 604/392 |
| 5,876,531 A | 3/1999 | Jacobs et al. | 156/66 |
| 5,897,545 A | 4/1999 | Kline et al. | 604/386 |
| 5,904,802 A | 5/1999 | Niedermeyer | |
| 5,916,203 A | 6/1999 | Brandon et al. | |
| 5,919,334 A | 7/1999 | Niedermeyer | |
| 5,944,707 A | 8/1999 | Ronn | |
| 5,961,761 A | 10/1999 | Heindel et al. | |
| 6,022,430 A | 2/2000 | Blenke et al. | |
| 6,022,431 A | 2/2000 | Blenke et al. | |
| 6,022,432 A | 2/2000 | Elsberg et al. | |
| 6,036,805 A | 3/2000 | McNichols | |
| 6,113,717 A | 9/2000 | Vogt et al. | |
| 6,149,638 A | 11/2000 | Vogt et al. | |

FOREIGN PATENT DOCUMENTS

| | | | |
|---|---|---|---|
| EP | 0 251 251 | 1/1988 | |
| EP | 0 463 276 | 1/1992 | |
| EP | 0532034 | * 3/1993 | 604/392 |
| EP | 0 544 703 | 6/1993 | |
| EP | 0 696 911 | 2/1996 | |
| EP | 0 753 292 | 1/1997 | |
| EP | 0 487 758 | 3/1997 | |
| EP | 0597331 | 11/1997 | |
| EP | 0 809 992 | 12/1997 | |
| EP | 0 878 180 A2 | 11/1998 | |
| FR | 2566631 | 3/1984 | |
| GB | 1 520 740 | 8/1978 | |
| GB | 2244422 | * 12/1991 | |
| GB | 2267024 | * 11/1993 | |
| GB | 2 288 314 | 10/1995 | |
| GB | 2 288 315 | 10/1995 | |
| GB | 2 288 316 | 10/1995 | |
| GB | 2 291 783 | 2/1996 | |
| GB | 2 294 867 | 5/1996 | |
| GB | 2 297 473 | 6/1996 | |
| GB | 2 308 290 | 6/1997 | |
| JP | 6-77718 | 11/1994 | |
| JP | 7-213553 | 8/1995 | |
| JP | 7-227407 | 8/1995 | |
| JP | 7-255773 | 10/1995 | |
| JP | 7-299094 | 11/1995 | |
| JP | 8-229072 | 9/1996 | |
| JP | 9-287 | 5/1997 | |
| JP | 11-47188 | 2/1999 | |
| WO | 83/04163 | 12/1983 | |
| WO | 90/07313 | 7/1990 | |
| WO | 91/04724 | 4/1991 | |
| WO | 91/08725 | 6/1991 | |
| WO | 92/22274 | 12/1992 | |
| WO | 93/09742 | 5/1993 | |
| WO | 94/17768 | 8/1994 | |
| WO | 95/01148 | 1/1995 | |
| WO | 95/02383 | 1/1995 | |
| WO | 95/13772 | 5/1995 | |
| WO | 95/22951 | 8/1995 | |
| WO | 95/27460 | 10/1995 | |
| WO | 95/27462 | 10/1995 | |
| WO | 95/29657 | 11/1995 | |
| WO | 96/03101 | 2/1996 | |
| WO | 96/18315 | 6/1996 | |
| WO | 96/29037 | 9/1996 | |
| WO | 96/32084 | 10/1996 | |
| WO | 97/15260 | 5/1997 | |
| WO | 97/23186 | 7/1997 | |
| WO | 97/25951 | 7/1997 | |
| WO | 97/31605 | 9/1997 | |
| WO | 97/32555 | 9/1997 | |
| WO | 97/33547 | 9/1997 | |
| WO | 97/46197 | 12/1997 | |
| WO | 97/47265 | 12/1997 | |
| WO | 97/48357 | 12/1997 | |
| WO | 98/03140 | 1/1998 | |
| WO | 98/18421 | 5/1998 | |
| WO | 98/29251 | 7/1998 | |
| WO | 98/51252 | 11/1998 | |
| WO | 98/56328 | 12/1998 | |
| WO | 99/07319 | 2/1999 | |
| WO | 99/56688 | 11/1999 | |
| WO | 99/65438 | 12/1999 | |
| WO | 99/65442 | 12/1999 | |
| WO | 00/37010 | 6/2000 | |

* cited by examiner

MULTI-FUNCTIONAL FASTENER FOR DISPOSABLE ABSORBENT ARTICLES

FIELD OF THE INVENTION

The present invention relates to disposable absorbent articles which are adapted to contain body exudates. More particularly, the present invention relates to disposable absorbent articles which have fastening systems to maintain the articles about the waist of the wearer.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers have typically included a front waist portion and a back waist portion which are releasably connected about the hips of the wearer using conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the outer surface of the outer cover of the diaper in the front waist portion of the diaper.

In such a configuration, the diaper has been positioned between the legs of the wearer and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the care giver. However, such conventional diapers typically are not capable of being pulled up or down over the hips of the wearer when the fasteners are attached.

Several attempts have been made to provide absorbent articles which effectively contain body exudates and are capable of being pulled up or down over the hips of the wearer. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to assist in removing the absorbent article from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. Moreover, the removal of soiled absorbent articles which have integral side panels, such as conventional training pants, has not been completely satisfactory. For example, the side panels have been difficult to tear when attempting to remove the article from the waist of the wearer instead of pulling the article down over the hips of the wearer. As a result, many of such articles have not contained bodily exudates as effectively as conventional diaper-type articles which can be adjusted to achieve a more conforming fit to the wearer.

Accordingly, despite the attempts to develop improved absorbent articles, there remains a need for absorbent articles which effectively contain bodily exudates, which are capable of being pulled up and down over the hips and buttocks of the wearer, and which are readily secured about and removed from the wearer in a convenient and clean manner. Moreover, there is a need for disposable absorbent articles which include waist sections which are releasably prefastened such that the article can be pulled on over the wearers legs and which include adjustable fasteners which can be easily adjusted about the waist of a wearer after the article has been pulled on.

SUMMARY OF THE INVENTION

In response to the difficulties and problems discussed above, a new disposable absorbent article which has an improved multi-functional fastening system has been discovered. In one aspect, the present invention concerns a prefastened disposable absorbent article comprising an absorbent, an interior surface configured to face a wearer's body in use, an outer surface opposite said interior surface, a front waist region, a back waist region, a crotch region which extends between and connects the waist regions and a pair of laterally opposed side edges. The prefastened absorbent article further includes a multi-functional fastening system which includes a pair of primary fasteners and a secondary fastener. The primary fasteners are respectively located on the opposed side edges in one of the waist regions of the article. The primary fasteners are refastenably prefastened to the outer surface in the waist region opposite the one of the waist regions of the disposable absorbent article to refastenably engage the front waist region to the back waist region during manufacture to define a waist perimeter dimension and to provide the prefastened disposable absorbent article. The secondary fastener is located in one of the waist regions and is configured to refastenably engage the outer surface in the waist region opposite the one of the waist regions to reduce the waist perimeter dimension and conform the waist regions to a wearer's body after the prefastened disposable absorbent article is pulled on over the wearer's hips.

In another aspect, the present invention concerns a disposable absorbent article comprising an absorbent, an interior surface configured to face a wearer's body in use, an outer surface opposite said interior surface, a front waist region, a back waist region, a crotch region which extends between and connects said the regions and a pair of laterally opposed side edges. The absorbent article further includes a multi-functional fastening system which includes a pair of primary fasteners, a belt segment and a pair of secondary fasteners. The primary fasteners are respectively located on the opposed side edges in one of the waist regions and are configured to outer surface in the waist region opposite the one of the waist regions refastenably engage of the disposable absorbent article to refastenably engage the front waist region to the back waist region. The belt segment is located in one of the waist regions and defines an attached portion which is secured to the waist region along an attached length which is less than about 50 percent of a total length of said belt segment and laterally opposed end portions. The secondary fasteners are respectively located on the opposed end portions of the belt segment. The secondary fasteners are configured to refastenably engage the outer surface in the waist region opposite the one of the waist regions to conform the waist regions to a wearer's body after the primary fasteners are refastenably engaged.

In yet another aspect, the present invention concerns a disposable absorbent article comprising an absorbent, an interior surface configured to face a wearer's body in use, an outer surface opposite said interior surface, a front waist region, a back waist region, a crotch region which extends between and connects the waist regions and a pair of laterally opposed side regions. The absorbent article includes an outer cover which provides said outer surface, an absorbent chassis and a multi-functional fastening system. The absorbent chassis includes a backsheet which is connected to the outer cover, a bodyside liner which is connected to the backsheet in a superposed relation and an absorbent core disposed between the backsheet and the bodyside liner. The multi-functional fastening system includes a pair of primary fasteners which are respectively located on the outer cover on the laterally opposed side edges of the back waist region of the absorbent article. The primary fasteners are configured to refastenably engage an outer surface of the absorbent article in the front waist region of the absorbent article in use. The fastening system also includes a belt segment which is located in the back waist region of the absorbent article and which defines an attached portion which is secured to the back waist region along an attached length which is less than about 50 percent of a total length of said belt segment and a pair of laterally opposed end portions. A pair of secondary fasteners are respectively located on the opposite end portions of the belt segment and are configured to refastenably engage the outer surface of the absorbent article in the front waist region to further conform the waist regions to a wearer's body after the primary fasteners are refastenably engaged. In a particular embodiment, the laterally opposed end portions of the belt segment extend through slots in the back waist region onto an outer surface of the absorbent article. Each of the secondary fasteners and the opposite end portions of the belt segment may be configured to extend over the respective primary fasteners to refastenably engage the front waist region.

In still another aspect, the present invention concerns a package of prefastened disposable absorbent articles including a container and a plurality of the prefastened disposable absorbent articles. The prefastened articles comprise an absorbent, an interior surface configured to face a wearer's body in use, an outer surface opposite said interior surface, a front waist region, a back waist region, a crotch region which extends between and connects the waist regions and a pair of laterally opposed side edges. Each of the prefastened disposable absorbent articles further includes a multi-functional fastening system which includes a pair of primary fasteners and at least one secondary fastener. The pair of primary fasteners are respectively located on the opposed side edges in one of the waist regions and are refastenably prefastened to the outer surface in the waist region opposite the one of the waist regions of the disposable absorbent article to refastenably engage the front waist region to the back waist region during manufacture to define a waist perimeter dimension and the prefastened absorbent articles. A secondary fastener is located in one of the waist regions. The secondary fastener is configured to refastenably engage the outer surface in the waist region opposite the one of the waist regions in use to reduce the waist perimeter dimension and conform the waist regions to a wearer's body after the prefastened disposable absorbent article is pulled on over the wearer's hips.

In yet another aspect, the present invention concerns a disposable absorbent article comprising an absorbent, an interior surface configured to face a wearer's body in use, an outer surface opposite said interior surface, a front waist region, a back waist region, a crotch region which extends between and connects the waist regions and a pair of laterally opposed side edges. The absorbent article further includes a multi-functional fastening system which comprises a pair of primary fasteners and a waist size adjustment means for reducing the waist perimeter dimension of the article after the primary fasteners have been refastenably engaged. The pair of primary fasteners are respectively attached to and located on the opposed side edges in one of the waist regions and are configured to refastenably engage the outer surface in the waist region opposite the one of the waist regions of the disposable absorbent article in use to refastenably engage the front waist region to the back waist region during manufacture thereby defining the waist perimeter dimension. The waist size adjustment means located in one of the waist regions and configured to refastenably engage the outer surface of the absorbent article in a waist region opposite the one of the waist regions is configured to reduce the waist perimeter dimension of the absorbent article without releasing the primary fasteners in use to conform the waist regions to a wearer's body after the primary fasteners are refastenably engaged to said outer surface in the opposite waist region to secure the absorbent article about a wearer's waist. In a particular embodiment, the primary fasteners are prefastened such that the absorbent article may be pulled on over the hips of the wearer. The waist size adjustment means may include at least one secondary fastener which is located in one of said the regions and which is configured to refastenably engage the opposite waist region.

The present invention advantageously provides an absorbent article which includes a multi-functional fastening system. The fastening system can be used to releasably engage the front and back waist portions of the absorbent article to maintain the absorbent article about the waist of the wearer in a similar manner to conventional diapers. The fastening system can also be prefastened to releasably engage the front and back waist portions to allow the absorbent article to be pulled up or down over the hips of the wearer such as conventional training pants. As a result, the absorbent article of the present invention is designed to conform to the body of the wearer to effectively contain bodily exudates while still being capable of being pulled up or down over the hips of the wearer to assist in the toilet training of the wearer. Moreover, the absorbent article of the present invention can advantageously be applied to and removed from the wearer with relative ease and cleanliness.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
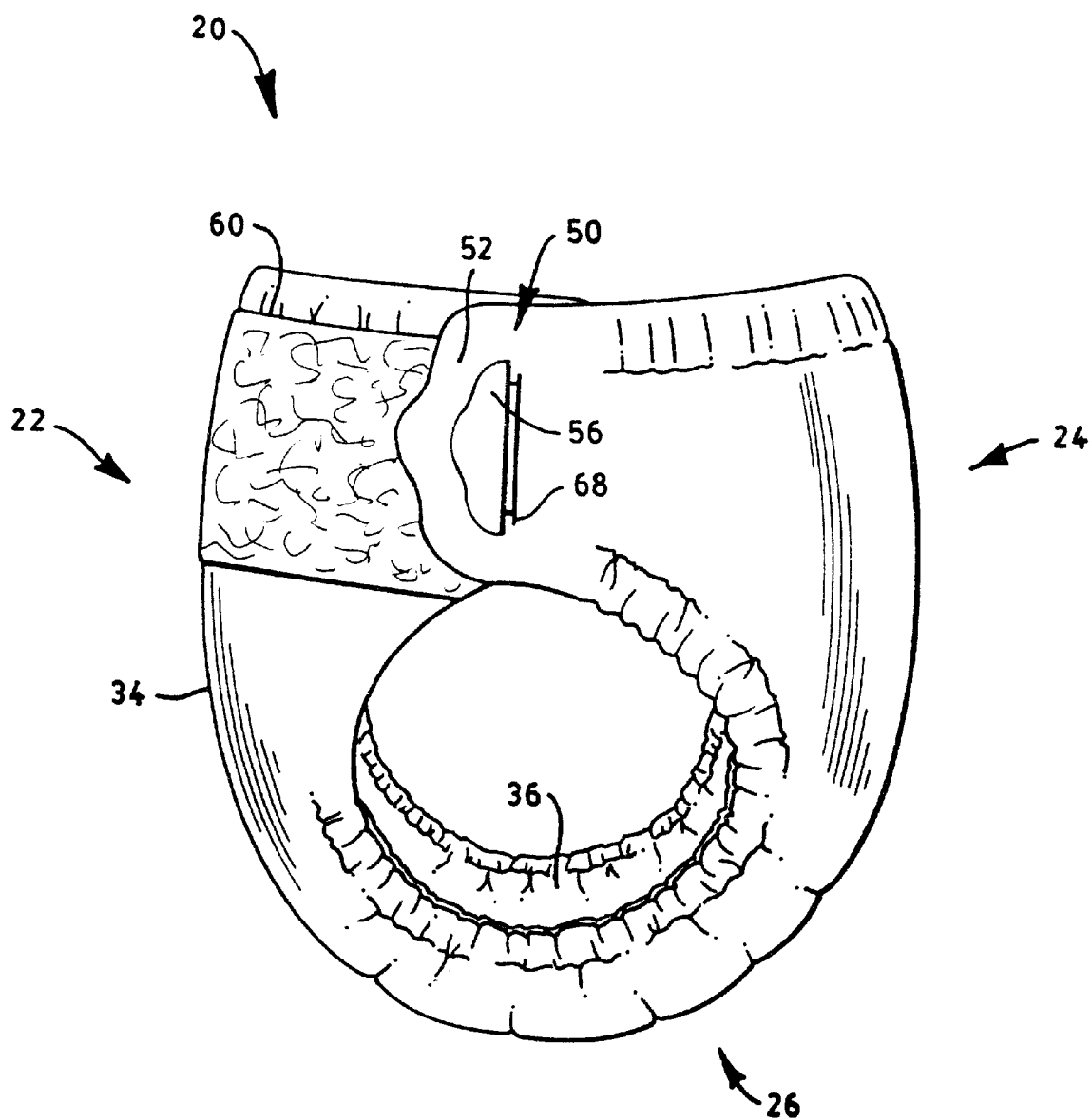
FIG. 1 representatively shows a side view of an example of a disposable absorbent article according to the present invention wherein the primary fasteners are in a prefastened configuration.
Figure 2:
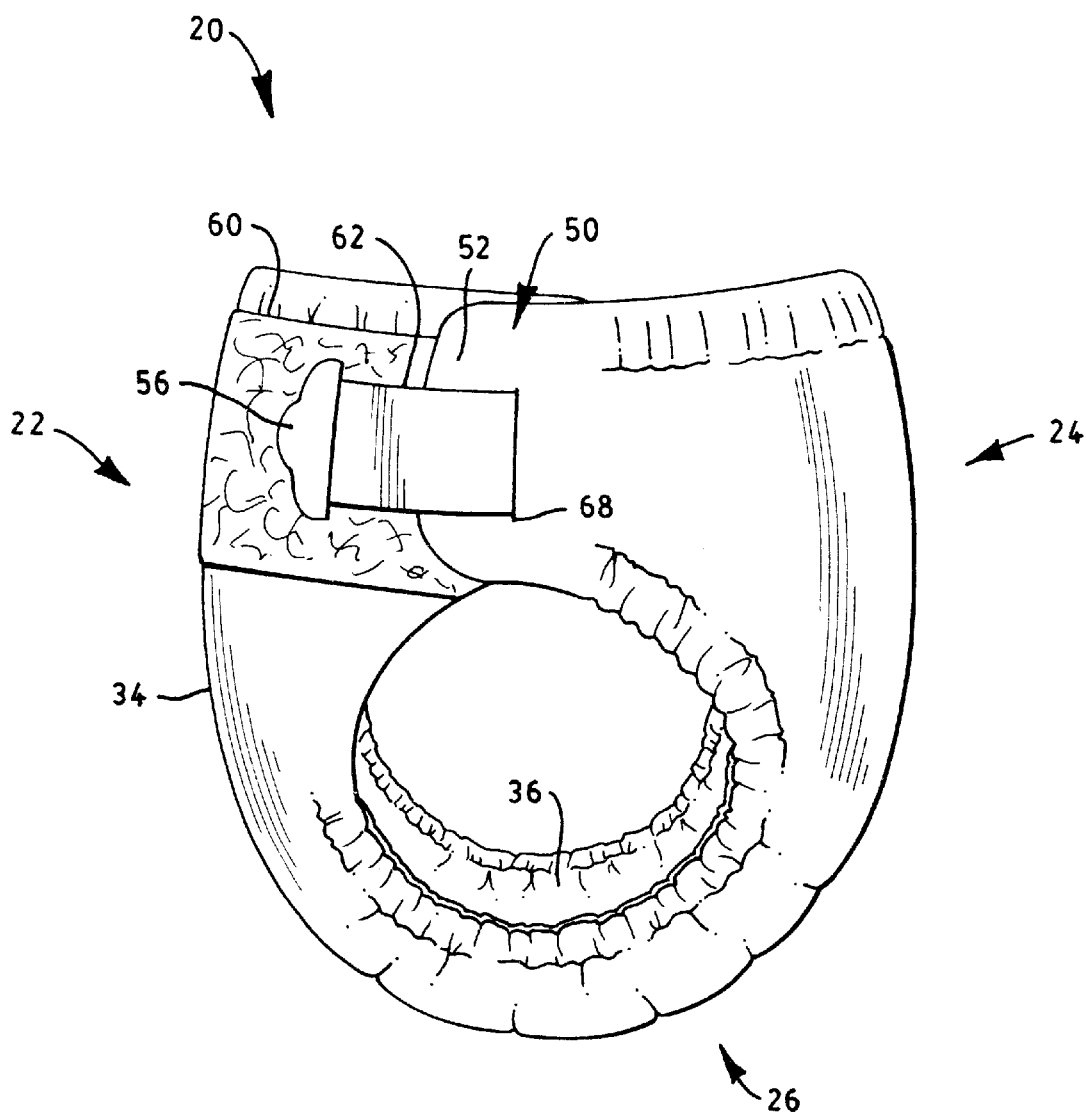
FIG. 2 representatively shows a side view of the disposable absorbent article of FIG. 1 wherein the secondary fasteners have been extended and engaged to conform the waist regions of the article to the waist of the wearer after the article has been pulled on over the hips of the wearer.

The present invention concerns disposable absorbent articles which are configured to closely conform to the body of the wearer to effectively contain body exudates while being capable of being pulled up or down over the hips and buttocks of the wearer. The disposable absorbent articles can also be easily secured to and removed directly from the waist of the wearer. The disposable absorbent articles are adapted to be worn adjacent to the body of a wearer to absorb and contain various exudates discharged from the body. As used herein, the term "disposable" refers to articles which are intended to be discarded after a limited use and which are not intended to be laundered or otherwise restored for reuse. The disposable absorbent articles of the present invention will be described in terms of a disposable diaper article which is adapted to be worn by infants about the lower torso. It is understood that the disposable absorbent articles of the present invention are equally adaptable for use as other types of absorbent articles such as adult incontinent products, training pants, feminine hygiene products, other personal care or health care garments, and the like.

FIGS. 1–4 representatively illustrate an example of a disposable diaper, as generally indicated at 20, according to the present invention. As representatively illustrated in FIGS. 1–4, the diaper 20 defines a front waist region 22, a back waist region 24, a crotch region 26 which extends between and connects the front and back waist regions 22 and 24, a pair of laterally opposed side edges 28, an interior surface 30 and an outer surface 32. The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. When the diaper 20 is intended to be worn by an infant weighing from about 22 to about 37 pounds, the crotch region 26 generally defines a length of from about 5 to about 15 centimeters.

The diaper 20 includes an outer cover 34, an absorbent chassis 36 and a multi-functional fastening system 50 which includes a pair of primary fasteners 52 and 54 and a pair of secondary fasteners 56 and 58. The absorbent chassis 36 is configured to contain and/or absorb any body exudates discharged from the wearer. Whereas, the outer cover 34 and multi-functional fastening system 50 are configured to maintain the diaper 20 about the waist of the wearer, conceal the absorbent chassis 36 from view, and provide a garment-like appearance. The diaper 20 may further include leg elastics 96 and 98 and containment flaps 100 and 102. It should be recognized that individual components of the diaper 20 may be optional depending upon the intended use of the diaper 20.

As representatively illustrated in FIGS. 1–4, the laterally opposed side edges 28 of the diaper 20 are generally defined by the side edges of the outer cover 34 which further define leg openings which may be curvilinear. The waist edges of the outer cover 34 also define a waist opening which is configured to encircle the waist of the wearer when worn. The outer cover 34 of the diaper 20 may suitably be composed of a material which is either liquid permeable or liquid impermeable. Since the absorbent chassis 36 of the different aspects of the present invention is designed to contain the body exudates discharged from the wearer, it is generally not necessary that the outer cover 34 be liquid impermeable. For example, the outer cover 34 may include various woven or nonwoven materials such as spunbond material, meltblown material, cotton material, rayon material or combinations thereof such as a spunbond-meltblown-spunbond (SMS) laminate material.

The outer cover 34 may otherwise be at least partially liquid impermeable to further prevent any leakage of body exudates. For example, a typical outer cover 34 can be manufactured from a thin plastic film or other flexible liquid-impermeable material. In a particular aspect, the outer cover 34 may be formed from a polyethylene film having a thickness of from about 0.012 millimeter (0.5 mil) to about 0.051 millimeter (2.0 mils). The outer cover 34 may also be formed of a woven or nonwoven fibrous web layer which has been totally or partially constructed or treated to impart a desired level of liquid impermeability to selected regions. Further, the outer cover 34 may optionally be composed of a micro-porous "breathable" material which permits vapors to escape from the diaper 20 while still preventing liquid exudates from passing through the outer cover 34. Still further, the outer cover 34 may also be an elasticized material such as a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference.

If it is desired to present the outer cover 34 with a more clothlike feeling, the outer cover 34 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). The outer cover 34 may otherwise be a stretch-thermal laminate (STL)

material which includes a film layer positioned between two spunbond layers and which has a basis weight of about 70–75 grams per square meter. The film layer may be composed of meltblown polypropylene fibers and the spunbond layers may be composed of polypropylene fibers. The outer cover 34 may also include bicomponent fibers such as polyethylene/polypropylene bicomponent fibers. Methods of forming such clothlike outer covers are known to those skilled in the art.

As representatively illustrated in FIGS. 1–4, the absorbent chassis 36 of the diaper 20 is suitably connected to the outer cover 34 to provide the disposable diaper 20. The absorbent chassis 36 may be connected to the outer cover 34 in manners well known to those skilled in the art. For example, the absorbent chassis 36 may be bonded to the outer cover 34 using adhesive, thermal or ultrasonic bonding techniques known to those skilled in the art. Alternatively, the absorbent chassis 36 may be connected to the outer cover 34 using conventional fasteners such as buttons, hook and loop type fasteners, adhesive tape fasteners, and the like. The other components of the diaper 20 may be suitably connected together using similar means.

Desirably, the absorbent chassis 36 is connected to the outer cover 34 only at or adjacent the waist edges of the outer cover 34 thereby creating a front attached portion, a back attached portion and an unattached portion which extends between and connects the attached portions. The unattached portion of the absorbent chassis 36 remains substantially unattached to the outer cover 34 and is generally configured to fit between the legs of the wearer and at least partially cover the lower torso of the wearer when in use. As a result, the unattached portion is generally the portion of the absorbent chassis 36 which is configured to initially receive the body exudates from the wearer when in use. In this manner, the absorbent chassis 36 is connected to the outer cover 34 in such a manner to secure the chassis 36 in place while not adversely restricting the movement of the outer cover 34 in use. Alternatively, the absorbent chassis 36 may be attached to the outer cover 34 along the entire longitudinal length of the absorbent chassis 36 or any portion thereof or along only the outer periphery of the absorbent chassis 36.

As representatively illustrated in FIGS. 1–4, the absorbent chassis 36 according to the present invention may include a backsheet 38, a bodyside liner 40 which is connected to he backsheet 38 in a superposed relation, and an absorbent core 42 which is located between the bodyside liner 40 and the backsheet 38. In alternative configurations wherein the outer cover 34 is at least partially resistant to the flow of liquids therethrough, the backsheet 38 may optionally be omitted from the absorbent chassis 36.

The absorbent chassis 36 is generally conformable and capable of absorbing and retaining body exudates. The absorbent chassis 36 may have any of a number of shapes and sizes. For example, as representatively illustrated in FIGS. 1–4, the absorbent chassis 36 may be rectangular, I-shaped or T-shaped. The size and absorbent capacity of the absorbent chassis 36 should be compatible with the size of the intended wearer and the fluid loading imparted by the intended use of the diaper 20. Typically, it is desirable that the absorbent chassis 36 have an absorbent capacity of at least about 300 grams of urine. It is generally preferred that the absorbent chassis 36 be narrower in the crotch region 26 than in the waist regions 22 and 24. It has been found that the absorbent chassis 36 of the present invention is particularly useful when the width dimension in the crotch region 26 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension of the absorbent chassis 36 allows the absorbent chassis 36 to better fit between the legs of the wearer.

The bodyside liner 40 of the absorbent chassis 36, as representatively illustrated in FIGS. 1–4, suitably presents a bodyfacing surface which is intended to be worn adjacent the body of the wearer and is compliant, soft feeling and nonirritating to the wearer's skin. Further, the bodyside liner 40 may be less hydrophilic than the absorbent core 42, to present a relatively dry surface to the wearer, and may be sufficiently porous to be liquid permeable, permitting liquid to readily penetrate through its thickness. A suitable bodyside liner 40 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 40 is suitably employed to help isolate the wearer's skin from fluids held in the absorbent core 42 of the absorbent chassis 36.

Various woven and nonwoven fabrics can be used for the bodyside liner 40. For 35 example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 40 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation TRITON X-102.

The backsheet 38 of the absorbent chassis 36, as representatively illustrated in FIGS. 1–4, may suitably be composed of a material which is either liquid permeable or liquid impermeable. It is generally preferred that the backsheet 38 be formed from a material which is substantially impermeable to fluids. A typical backsheet can be manufactured from a thin plastic film or other flexible liquid-impermeable material. For example, the backsheet 38 may be formed from a polyethylene film having a thickness of from about 0.012 millimeter (0.5 mil) to about 0.051 millimeter (2.0 mils). The backsheet 38 may also comprise a film layer having a nonwoven web laminated to the outer surface thereof, such as a spunbond web of polyolefin fibers. The backsheet 38 may also be constructed of a material which is similar to the material comprising the outer cover 34, such as an STL material. Further, the backsheet 38 may be formed of a woven or nonwoven fibrous web layer which has been totally or partially constructed or treated to impart a desired level of liquid impermeability to selected regions that are adjacent or proximate the absorbent core 42. Still further, the backsheet 38 may optionally be composed of a micro-porous "breathable" material which permits vapors to escape from the absorbent core 42 while still preventing liquid exudates from passing through the backsheet 38. For example, the backsheet 38 may be a breathable polyethylene film material commercially available from Exxon Chemical Patents, Incorporated, a business having offices located in Linden, N.J., under the trade designation EXXAIRE. In such a configuration, it is desirable that the outer cover 34 also comprise such a breathable material.

The bodyside liner 40 and backsheet 38 are generally adhered to one another so as to form a pocket in which the absorbent core 42 is located to provide the absorbent chassis 36. The bodyside liner 40 and backsheet 38 may be adhered directly to each other around the outer periphery of the absorbent chassis 36 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 40 to the backsheet 38. It should be noted that both the bodyside liner 40 and the backsheet 38 need not extend completely to the outer periphery of the absorbent chassis 36. For example, the backsheet 38 may extend to the outer periphery of the absorbent chassis 36 while the bodyside liner 40 may be attached to the backsheet 38 inboard of the outer periphery of the absorbent chassis 36, or more towards the longitudinal centerline of the diaper 20. In alternative configurations, especially wherein the backsheet 38 is omitted, the bodyside liner 40 may be suitably adhered directly to the absorbent core 42 or to the outer cover 34.

The absorbent core 42, as representatively illustrated in FIGS. 1–4, is positioned between the bodyside liner 40 and the backsheet 38 to form the absorbent chassis 36. The absorbent core 42 is desirably conformable and capable of absorbing and retaining body exudates. The absorbent core 42 may have any of a number of shapes and sizes. For example, the composite absorbent core may be rectangular, I-shaped or T-shaped. It is generally preferred that the absorbent core 42 be narrower in the crotch region 26. The size of the absorbent core 42 should be compatible with the size of the intended wearer and the desired absorbent capacity of the absorbent chassis 36.

The absorbent core 42 of the absorbent chassis 36 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 42 may also comprise selected blends of the various types of fibers mentioned above.

In a particular aspect of the invention, the absorbent core 42 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 42 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 42 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va. Other suitable high-absorbency materials may include superabsorbent polymers which are commercially available from Dow Chemical Corp., a business having offices in Midland, Mich.

As a general rule, the high-absorbency material is present in the absorbent core 42 of the present invention in an amount of from about 5 to about 95 weight percent and desirably from about 10 to about 60 weight percent based on the total weight of the absorbent core 42. The distribution of the high-absorbency material within the different portions of the absorbent core 42 can vary depending upon the intended end use of the absorbent core 42.

As representatively illustrated in FIGS. 1–4, the absorbent chassis 36 of the disposable diaper 20 may include a pair of containment flaps 100 and 102 which are configured to provide a barrier to the lateral flow of body exudates. The containment flaps 100 and 102 may be located along the laterally opposed side edges of the absorbent chassis 36. Each containment flap defines an attached edge 104 and an unattached edge 106. Each of the containment flaps 100 and 102 may also include at least one elongated elastic member 108 which is adhered to the unattached edge 106 of the containment flap 100 and 102 and configured to gather the unattached edge 106 and form a seal against the body of the wearer when in use. The containment flaps 100 and 102 may extend longitudinally along the entire length of the absorbent chassis 36 or may only extend partially along the length of the absorbent chassis 36. When the containment flaps 100 and 102 are shorter in length than the absorbent chassis 36, the containment flaps 100 and 102 can be selectively positioned anywhere along the side edges of the absorbent chassis 36. In a particular aspect of the invention, the containment flaps 100 and 102 extend along the entire length of the absorbent chassis 36 to better contain the body exudates.

The containment flaps 100 and 102 can be made from any material which provides the desired barrier against the flow of body exudates. For example, the containment flaps 100 and 102 may be constructed of a material which is similar to the material comprising the outer cover 34. Other conventional materials, such as polymeric films, may also be employed. In a particular aspect, the containment flaps 100 and 102 may be constructed of a STL material having a basis weight of about 70–75 grams per square meter and comprising a meltblown layer of meltblown polypropylene fibers between two spunbond layers of polypropylene fibers.

Each containment flap 100 and 102 is attached to the side edges of the absorbent chassis 36 such that the containment flaps 100 and 102 provide a barrier to the lateral flow of body exudates. The attached edge 104 of each of the containment flaps 100 and 102 is attached to the side edges of the absorbent chassis 36 while the unattached edge 106 remains unattached from the absorbent chassis 36 in at least the crotch region 26 of the diaper 20. The attached edge 104 of the containment flaps 100 and 102 may be attached to the absorbent chassis 36 in any of several ways which are well known to those skilled in the art. For example, the attached edge 104 of the flaps 100 and 102 may be ultrasonically bonded, thermally bonded or adhesively bonded to the absorbent chassis 36. In a particular aspect, the unattached edge 106 of each of the containment flaps 100 and 102 remains unattached from the side edges of the absorbent chassis 36 along substantially the entire length of the unattached edge 106 to provide improved performance.

Alternatively, as representatively illustrated in FIGS. 1–4, the containment flaps 100 and 102 may be integral with the backsheet 38 or bodyside liner 40 of the absorbent chassis 36. For example, the containment flaps 100 and 102 may be composed of portions of the backsheet 38 which extend laterally beyond the side edges of the absorbent core 42 of the absorbent chassis 36.

Each containment flap 100 and 102 is also configured such that the unattached edge 106 of the containment flaps 100 and 102 tends to position itself in a spaced relation away from the absorbent chassis 36 toward a generally upright and perpendicular configuration, especially in the crotch region 26 when in use. As representatively illustrated in FIGS. 1–4, the unattached edge 106 of each containment flap 100 and 102 is desirably spaced away from the absorbent chassis 36 when in use thereby providing a barrier to the lateral flow of body exudates. Desirably, the unattached edge 106 of each containment flap 100 and 102 maintains a contacting relationship with the body of the wearer while the absorbent chassis 36 may be spaced away from the body of the wearer when in use. Typically, an elastic member 108 is attached to the unattached edge 106 of each containment flap 100 and 102 to maintain the spaced away relationship between the unattached edge 106 and the absorbent chassis 36. For example, the elastic member 108 may be attached to the unattached edge 106 in an elastically contractible condition such that the contraction of the elastic member 108 gathers or contracts and shortens the unattached edge 106 of the containment flap 100 and 102.

Materials suitable for use as the elastic member 108 of the containment flaps 100 and 102 are known to those skilled in the art. Exemplary of such materials are sheets, strands or ribbons of a polymeric, elastomeric material which are adhered to the flaps 100 and 102 in a stretched condition, or which are attached to the flaps 100 and 102 while the flaps are pleated, such that elastic constrictive forces are imparted to the flaps. The elastic member 108 may also include such materials as polyurethane, synthetic and natural rubber. In a particular aspect of the invention, the elastic members 108 may be composed of a plurality of individual strands of 620 decitex LYCRA which are commercially available from E. I. DuPont de Nemours Co. The containment flaps 100 and 102 may include from about 1 to about 10 elastic strands along the unattached edge 106. The elastic members 108 may be elongated prior to being attached to the unattached edge 106 of the containment flaps 100 and 102. For example, the elastic members 108 may be elongated at least about 75 percent and desirably from about 100 to about 150 percent before being attached such that the elastic members 108 gather the unattached edge 106 of the containment flaps 100 and 102. Desirably, the elastic members 108 are configured to gather and maintain the unattached edge 106 in a contacting relationship with the wearer's body when in use to effectively provide a seal against the lateral flow of body exudates.

Alternative constructions and arrangements for containment flaps 100 and 102 are described in U.S. Pat. No. 4,704,116 issued Nov. 3, 1987, to K. Enloe the disclosure of which is hereby incorporated by reference in a manner that is consistent herewith.

The absorbent article of the different aspects of the present invention further includes a multi-functional fastening system 50 for securing the absorbent article about the waist of the wearer. The multi-functional fastening system includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer.

As representatively illustrated in FIGS. 1–4, the multi-functional fastening system 50 of the present invention includes a pair of primary fasteners 52 and 54 which are located on the side edges 28 of the diaper 20 in the back waist region 24 of the diaper 20. In such a configuration, the primary fasteners 52 and 54 are configured to encircle the hips of the wearer and engage the outer surface 32 of the front waist region 22 of the diaper 20 to maintain the diaper 20 on the wearer. Alternatively, the primary fasteners 52 and 54 may be located on the front waist region 22 and may be configured to releasably engage the outer surface 32 of the back waist region 24 of the diaper 20.

Figure 3:
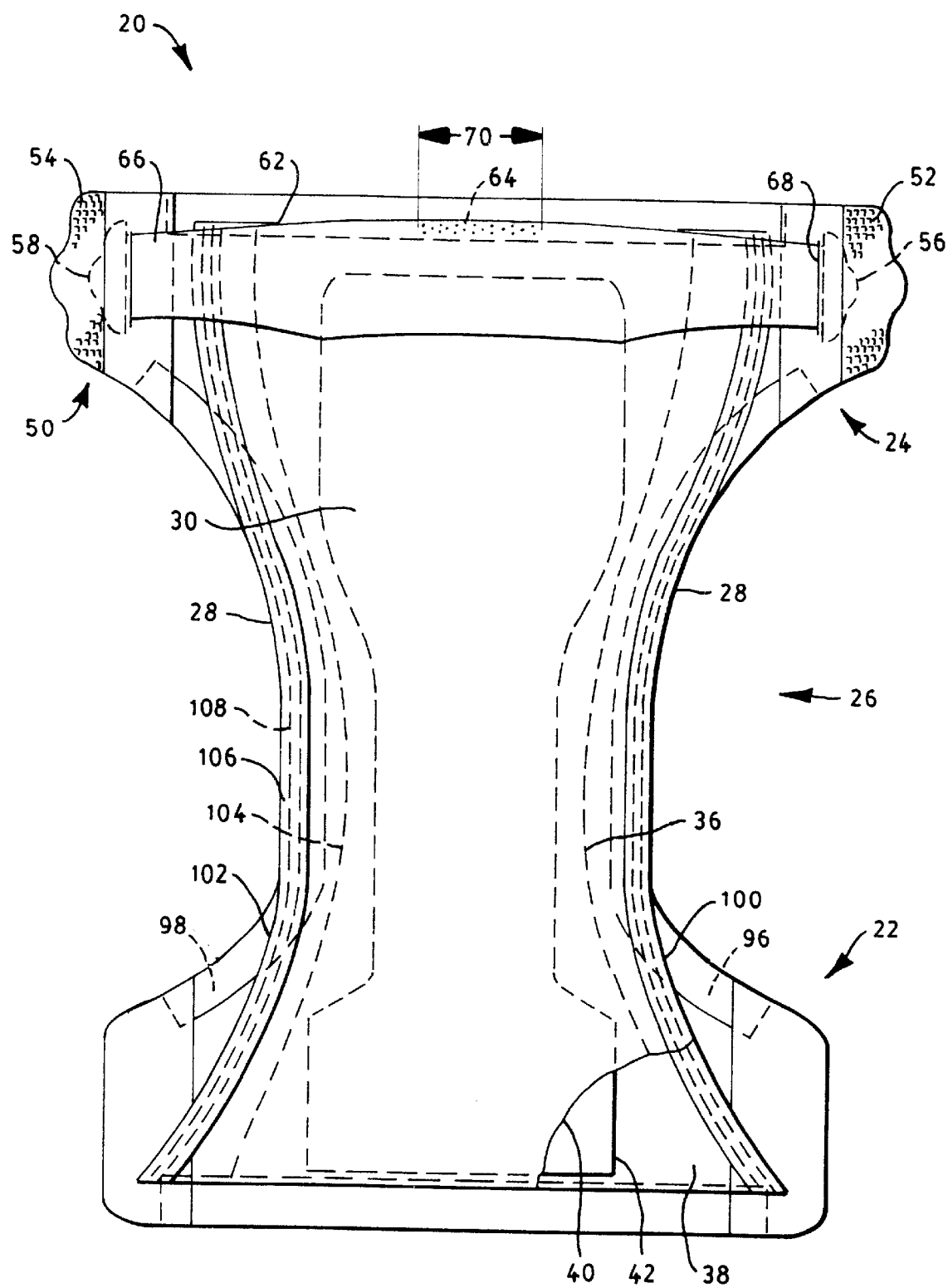
FIG. 3 representatively shows a plan view of the disposable absorbent article of FIG. 1 in a stretched and laid flat condition with the surface of the article which contacts the wearer facing the viewer; and with portions of the article cut away to more clearly show the underlying features.
Figure 4:
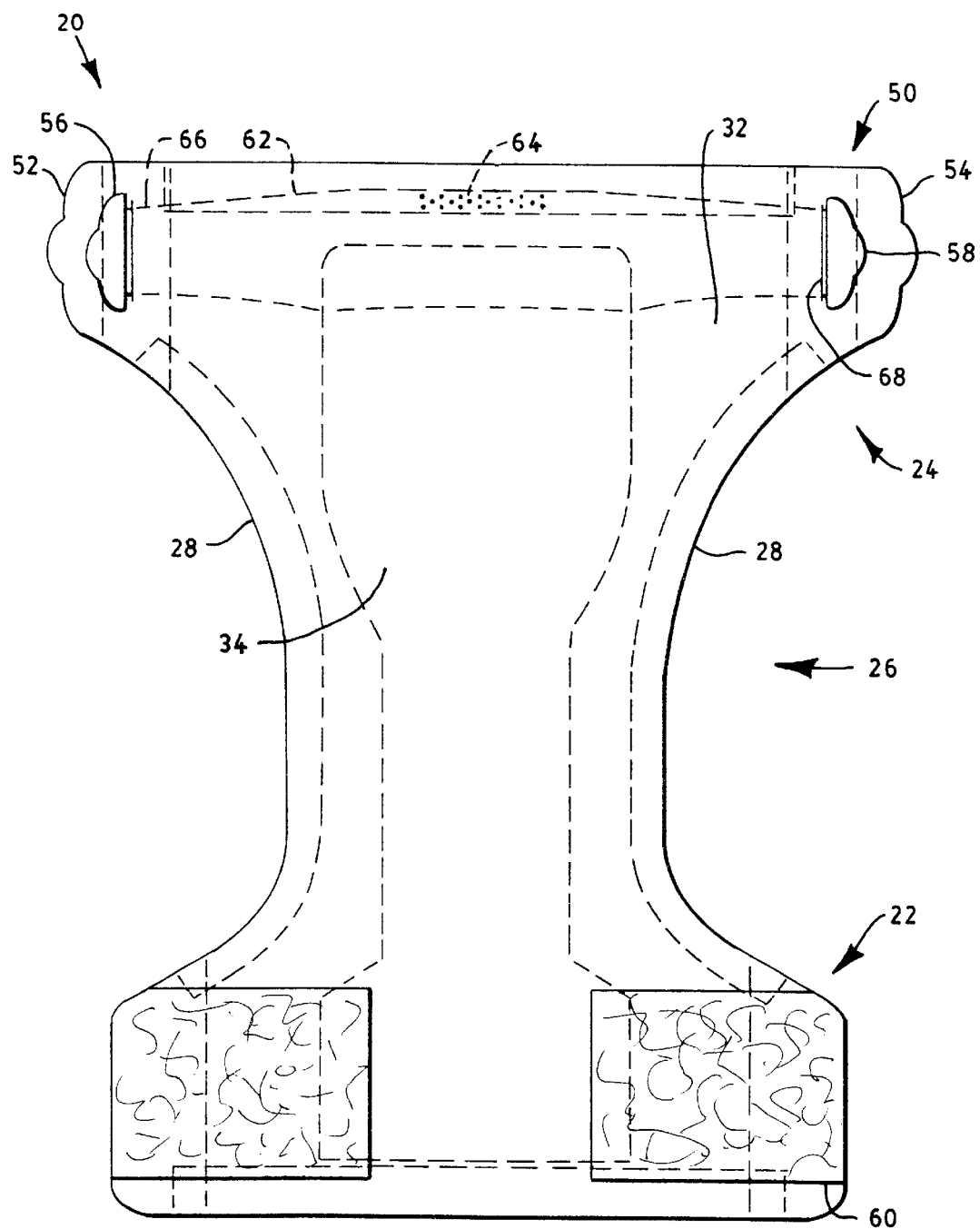
FIG. 4 representatively shows a plan view of the disposable absorbent article of FIG. 1 in a stretched and laid flat condition with the surface of the article which contacts the wearer's clothing facing the viewer.

Desirably, the primary fasteners 52 and 54 are releasably engageable directly with the outer surface of the outer cover 34 of the diaper 20 to provide improved ease of fastening. Alternatively, as representatively illustrated in FIGS. 1–4, the disposable diaper 20 of the present invention may further include an attachment panel 60 located on the outer cover 34 in one of the waist regions 22 and 24 of the diaper 20. In such a configuration, the primary fasteners 52 and 54 are releasably engageable with the attachment panel 60 to maintain the diaper 20 about the waist of the wearer. When the primary fasteners 52 and 54 are releasably engaged, the side edges 28 of the diaper 20 define leg openings which are configured to encircle the legs of the wearer and the waist regions 22 and 24 define a waist opening which is configured to encircle the waist of the wearer. As illustrated in FIG. 4, the attachment panel 60 may include two separate panels located along the opposite side edges in one of the waist regions 22 and 24 of the diaper 20. Alternatively, the attachment panel 60 may include a single piece of material which extends substantially across the respective waist region of the diaper 20.

In a particular embodiment, the primary fasteners 52 and 54 are configured to be releasably engaged with the outer surface of the opposite waist region 22 and 24 of the diaper 20 before the diaper 20 is placed on the wearer to provide a prefastened diaper.

In such a configuration, the prefastened diaper 20 can be pulled on or off over the legs and hips of the wearer. If the diaper 20 becomes soiled during use, the primary fasteners 52 and 54 can be disengaged to easily remove the diaper 20 from the waist of the wearer with reduced risk of undesirably soiling the clothes or legs of the wearer. Thus, in such a configuration, the diaper 20 of the different aspects of the present invention can be configured to be pulled on or off over the hips of the wearer such as conventional training pants and can be removed by disengaging the fasteners similar to conventional diaper articles.

The multi-functional fastening system 50 on the disposable diaper 20 of the present invention further includes at least one secondary fastener to provide improved securement of the diaper 20 about the waist of the wearer after the primary fasteners 52 and 54 have been releasably engaged. The secondary fastener of the present invention is configured to further conform the waist regions 22 and 24 of the diaper 20 to the waist of the wearer. For example, as representatively illustrated in FIGS. 1–4, the diaper 20 may include a pair of secondary fasteners 56 and 58 which are located on the side edges 28 in one of the waist regions 22 and 24 of the diaper 20. The secondary fasteners 56 and 58 are configured to encircle the hips of the wearer and engage the outer surface 32 in the opposite waist region 22 and 24 of the diaper 20. The secondary fasteners 56 and 58 may be located on the side edges 28 of the diaper 20 in the back waist region 24 of the diaper 20. In such a configuration, the secondary fasteners 56 and 58 are also configured to encircle the hips of the wearer and engage the outer surface 32 of the front waist region 22 of the diaper 20 to maintain the diaper 20 on the wearer. Alternatively, the secondary fasteners 56 and 58 may be located on the front waist region 22 and may be configured to releasably engage the outer surface 32 of the back waist region 24 of the diaper 20.

Desirably, the secondary fasteners 56 and 58 are releasably engageable directly with the outer surface of the outer cover 34 of the diaper 20 to provide improved ease of fastening. Alternatively, as described above and representatively illustrated in FIGS. 1–4, the diaper 20 of the present invention may further include an attachment panel 60 located on the outer cover 34 in one of the waist regions 22 and 24 of the diaper 20. In such a configuration, the secondary fasteners 56 and 58 may also be releasably engageable with the attachment panel 60 to maintain the diaper 20 about the waist of the wearer.

The use of such a secondary fastener has been found to be particularly desirable when the primary fasteners 52 and 54 are releasably engaged with the respective waist region of the diaper 20 to provide a prefastened diaper which can be pulled on over the legs and hips of the wearer. In such a configuration, the waist opening of the diaper 20 when the primary fasteners 52 and 54 are engaged must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer which may undesirably result in leaks. In such a configuration, the secondary fastener of the diaper 20 of the present invention is configured to conform the waist regions of the diaper 20 to the wearer after the prefastened diaper is pulled on the wearer. Thus, the care giver is not required to reposition the primary fasteners 52 and 54 to conform the waist regions 22 and 24 to the waist of the wearer. As a result, when the diaper 20 is to be removed from the wearer, the care giver may simply disengage the secondary fastener if necessary and pull the prefastened diaper down over the hips and legs of the wearer without having to reposition the primary fasteners 52 and 54.

In such configurations, the secondary fasteners 56 and 58 are intended to maintain the diaper 20 in a close conforming fit about the waist of the wearer to reduce the leakage of body exudates when in use. The primary fasteners 52 and 54 are intended to maintain the front and back waist regions 22 and 24 of the diaper 20 connected in such a manner that the diaper 20 can be pulled on or off over the hips of the wearer after the secondary fasteners 56 and 58 have been disengaged. The secondary fasteners 56 and 58 may also be selective disengaged to facilitate inspection of the diaper 20 to determine if it has been soiled. The primary fasteners 52 and 54 can also provide a "childproofing function" by maintaining the diaper 20 at least partially secured about the waist of the wearer if the wearer disengages the secondary fasteners 56 and 58.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIGS. 1–4, the primary fasteners 52 and 54 and secondary fasteners 56 and 58 may be hook type fasteners and the outer cover 34 or attachment panel 60 may be configured to function as a complimentary loop type fastener. Desirably, the fasteners 52, 54, 56 and 58 are hook type fasteners which are releasably engageable with the outer cover 34. Such an arrangement provides the ability to vary the size of the waist opening in very small increments over a wide range to fit the waist of the wearer. The fasteners may have any shape and size which provides the desired fastening of the diaper 20 about the waist of the wearer. It is further desirable that the outer surface of the secondary fasteners 56 and 58 provide a visual cue to the care giver as to their location. For example, in one embodiment, the secondary fasteners 56 and 58 are of a different color than the outer surface of the diaper 20 to enable the care giver to easily determine the location of the secondary fasteners 56 and 58.

In the illustrated embodiments, the primary fasteners 52 and 54 are attached directly to the side edges 28 of the diaper 20 in one of the waist regions 22 and 24. The primary fasteners 52 and 54 may be adhered to the side edges 28 by any means known to those skilled in the art such as adhesive bonds, sonic bonds or thermal bonds.

The secondary fasteners 56 and 58 may suitably be secured to the diaper 20 in any manner which provides the desired improved securement and conformance of the waist regions 22 and 24 of the diaper 20 about the waist of the wearer after the primary fasteners 52 and 54 have been releasably engaged. For example, as representatively illustrated in FIGS. 1–4, the diaper 20 of the different aspects of the present invention may further include a belt segment 62 located in one of the waist regions 22 and 24 of the diaper 20. The belt segment 62 defines an attached portion 64 which is secured to the respective waist region 22 and 24 of the diaper 20 and a pair of laterally opposed end portions 66. The secondary fasteners 56 and 58 are connected to the end portions 66 of the belt segment 62. In such a configuration, the end portions 66 of the belt segment 62 are configured to encircle the hips of the wearer such that the secondary fasteners 56 and 58 can releasably engage the opposite waist region to provide the improved fit of the diaper on the wearer after the primary fasteners have been engaged.

To provide the improved fit about the waist of the wearer without adversely affecting the appearance of the outer cover 34 of the diaper 20, the majority of the length of the belt segment 62 desirably is positioned along the interior surface 30 of the diaper 20 in the respective waist region 22 and 24. In such a configuration as representatively illustrated in FIGS. 1–4, the diaper 20 further includes a pair of slots 68 through which the end portions 66 of the belt segment 62 slidably extends. Thus, the end portions 66 of the belt segment 62 and the secondary fasteners 56 and 58 are located on the outer surface 32 of the diaper and the remaining portion of the belt segment 62 extends through to and along the interior surface 30 of the diaper 20 between the diaper and the wearer. As illustrated, the secondary fasteners 56 and 58 are desirably configured to releasably engage the outer surface 32 of the diaper 20 adjacent the slots 68 for improved control and ease of fastening.

The slots 68 may be provided by any means known to those skilled in the art. For example, the slots 68 may be provided by cutting the diaper 20 after it has been assembled together. Alternatively, the slots 68 may be provided by adding a segment of material to the side edges 28 of the diaper 20 which extends laterally outward from the side edges 28 while only attaching the segment of material to the side edges at its longitudinal ends. In such a configuration, the segment of material provides a slot between the side edge of the diaper and the segment of material for improved manufacturability.

In such a configuration, a portion of the belt segment 62 between the slots 68 is secured to the interior surface 30 of the diaper 20 to provide an attached portion 64. The attached portion 64 of the belt segment 62 may be secured to the interior surface of the diaper using methods known to those skilled in the art such as adhesive, sonic or thermal bonding. Desirably, the attached portion 64 defines an attached length 70 as illustrated in FIG. 3 which is less than about 75 percent and more desirably less than about 50 percent of the total length of the belt segment 62. Such an attached length provides sufficient securement of the belt segment to the diaper 20 without adversely affecting the ability of the belt segment to conform to the waist of the wearer to provide the improved fit.

The belt segment 62 may define any length and width which provide the desired improved fastening and fit about the wearer. For example, the belt segment 62 may define a length which is from about 7 to about 35 centimeters and a width which is from about 1 to about 10 centimeters. Desirably, the belt segment 62 defines a length which is slightly less than the width of the diaper 20 at the respective waist region such that the belt segment 62 is slightly elongated to pretension the waist region.

Figure 5:
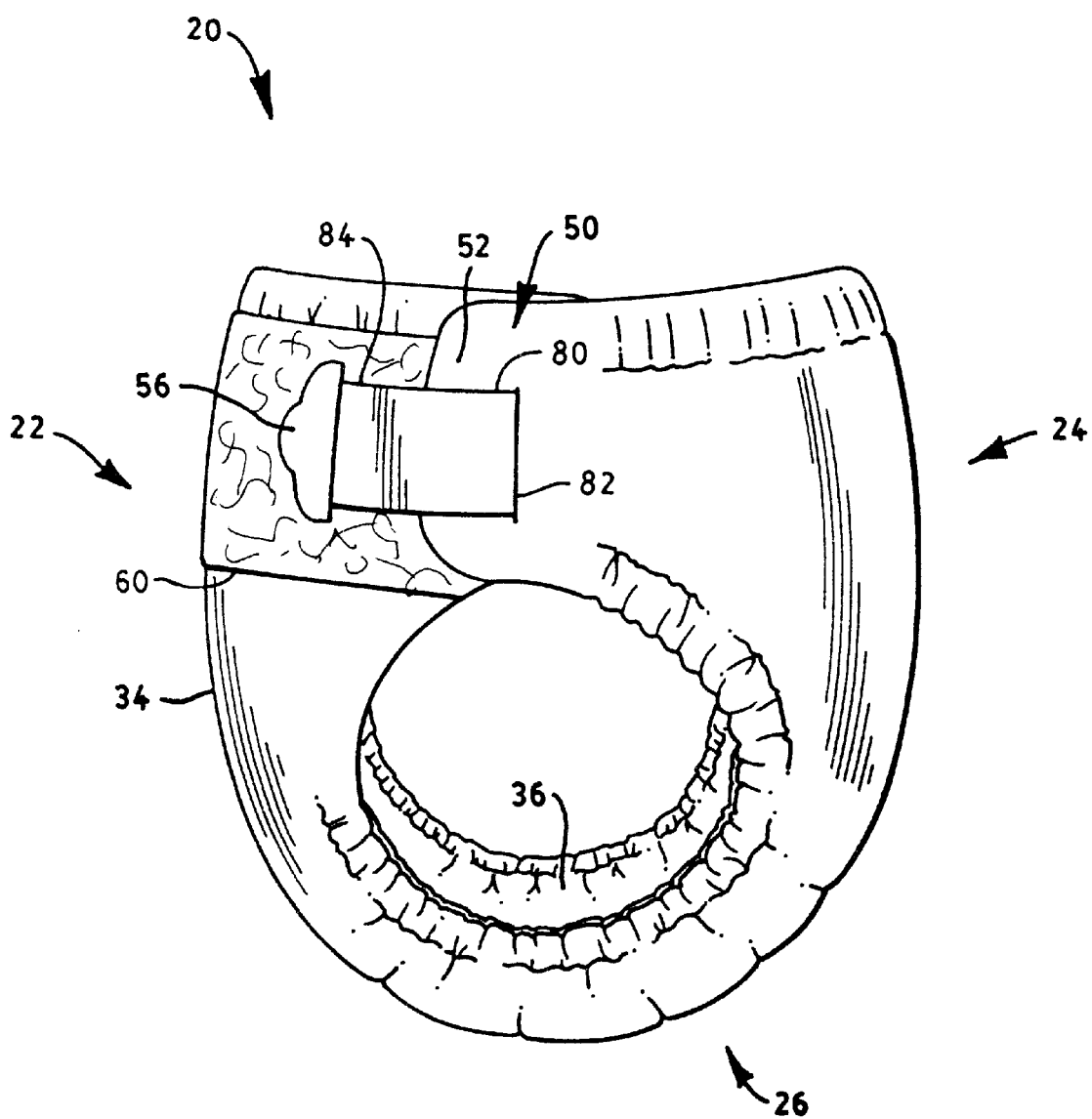
FIG. 5 representatively shows a side view of another example of a disposable absorbent article according to the present invention wherein the secondary fastener has been extended and engaged to conform the waist regions of the article to the waist of the wearer after the primary fasteners have been engaged.

Alternatively, as representatively illustrated in FIG. 5, the diaper 20 of the present invention may include at least one extension member 80 to which the secondary fastener 56 is attached. The extension member 80 defines an attached end 82 which is secured to the outer surface 32 of the diaper 20 and a free end 84 to which the secondary fastener 56 is attached. In such a configuration, the secondary fastener 56 and free end 84 of the extension member 80 are configured to encircle the hips of the wearer such that the secondary fastener 56 can releasably engage the opposite waist region to provide the improved fit of the diaper on the wearer after the primary fasteners 52 and 54 have been engaged.

Desirably, the attached end 82 of the extension member 80 is located inward from the primary fasteners 52 and 54. In such a configuration, the secondary fastener 56 and free end 84 of the extension member 80 are configured to extend over one of the primary fasteners to releasably engage the opposite waist region of the diaper to conform the waist regions to the wearer's body. The attached end 82 may be secured to the diaper 20 and the secondary fastener 56 may be secured to the free end 84 using suitable means described above. The extension member 80 may define any length and width which provide the desired improved fastening and fit about the wearer. For example, the extension member 80 may define a length which is from about 1 to about 15 centimeters and a width which is from about 1 to about 10 centimeters.

Materials suitable for use as the belt segment 62 or extension member 80 of the different aspects of the present invention are similar to those materials described above as being suitable for the outer cover 34. Desirably, the belt segment 62 or extension member 80 are made of an elastic material which is capable of elongating at least about 100 percent and more desirably at least about 130 percent to provide improved fit about the waist of the wearer. For example, the belt segment 62 may comprise a neck bonded laminate material which includes a KRATON film material commercially available from the Dow Chemical Company, a business having offices located in Midland, Mich. Alternatively, the belt segment 62 may include portions which include elastic material and portions which include inelastic material.

The disposable diaper 20 of the different aspects of the present invention may further include elastics at the waist edges and side edges 28 of the diaper 20 to further prevent the leakage of body exudates and support the absorbent chassis 36. For example, as representatively illustrated in FIGS. 1–4, the diaper 20 of the present invention may include a pair of leg elastic members 96 and 98 which are connected to the laterally opposed side edges 28 in the crotch region 26 of the diaper 20. The leg elastics 96 and 98 are generally adapted to fit about the legs of a wearer in use to maintain a positive, contacting relationship with the wearer to effectively reduce or eliminate the leakage of body exudates from the diaper 20.

Materials suitable for use as the leg elastics 96 and 98 are well known to those skilled in the art. Exemplary of such materials are sheets or strands or ribbons of a polymeric, elastomeric material which are adhered to the outer cover 34 in a stretched position, or which are attached to the outer cover 34 while the outer cover is pleated, such that elastic constrictive forces are imparted to the outer cover 34. The leg elastics may also include such materials as polyurethane, synthetic and natural rubber. In a particular aspect of the invention, the elastics may be composed of individual strands of 620 decitex LYCRA which are commercially available from E. I. DuPont de Nemours Co. When individual strands of elastic are used, the waist and leg elastics may include any suitable number of elastic strands to provide containment of the body exudates. For example, the leg elastics 96 and 98 may include from about 1 to about 10 elastic strands.

The leg elastics may be elongated prior to being attached to the outer cover 34. For example, the leg elastics may be elongated at least about 150 percent and desirably from about 200 to about 500 percent before being attached such that the elastics gather the outer cover 34 when relaxed. The leg elastics 96 and 98 may be joined to the outer cover 34 by any means known to those skilled in the art. For example, adhesive, thermal or ultrasonic bonding techniques or a combination thereof may be used to join the elastics to the outer cover. A suitable adhesive includes Findley H-2096 hot melt adhesive which is commercially available from Findley Adhesives, Inc.

Figure 6:
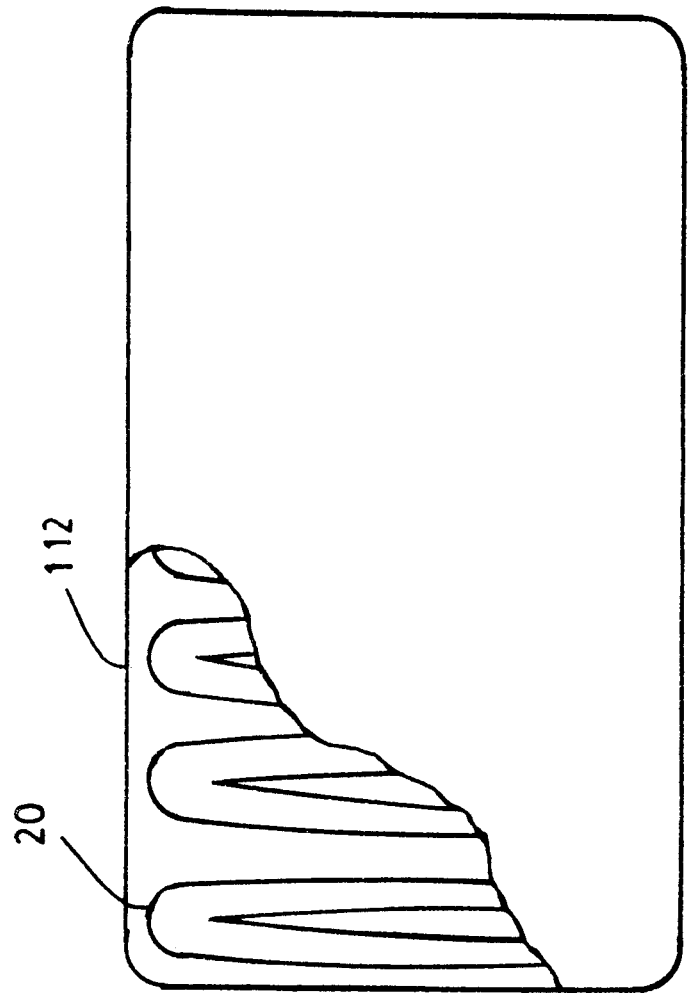
FIG. 6 representatively shows a package containing a plurality of the disposable absorbent articles of FIG. 1 with portions of the package cut away to show the absorbent articles contained therein.

In another aspect, the present invention provides a package of the diapers described above wherein the primary fasteners 52 and 54 have been engaged with the opposite waist region to provide prefastened disposable diapers. The package as representatively illustrated in FIG. 6 at 110 includes a container such as, for example, a plastic bag 112, and a plurality of prefastened disposable diapers. As described above, the prefastened diaper 20 includes at least one secondary fastener 56 which is located in one of the waist regions 22 and 24 of the diaper 20. The secondary fastener 56 is configured to releasably engage the opposite waist region to conform the waist regions 22 and 24 to the wearer's body after the prefastened disposable diaper is pulled on over the wearer's hips. Such a package provides diapers which can be pulled on over the legs of the wearer and which can be easily removed from the waist of the wearer after they have been soiled.

The different aspects of the present invention can advantageously provide an absorbent article which includes a multi-functional fastening system. The fastening system can be used to releasably engage the front and back waist portions of the absorbent article to maintain the absorbent article about the waist of the wearer in a similar manner to conventional diapers. The fastening system can also be prefastened to releasably engage the front and back waist portions to allow the absorbent article to be pulled up or down over the hips of the wearer such as conventional training pants. As a result, the absorbent article of the present invention is designed to conform to the body of the wearer to effectively contain bodily exudates while still being capable of being pulled up or down over the hips of the wearer to assist in the toilet training of the wearer. Moreover, the absorbent article of the present invention can advantageously be applied to and removed from the wearer with relative ease and cleanliness.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A package of prefastened disposable absorbent articles comprising a container and a plurality of the prefastened disposable absorbent articles which comprise an interior surface configured to face a wearer's body in use, an outer surface opposite the interior surface, an absorbent, a front waist region, a back waist region, a crotch region which extends between and connects the waist regions and a pair of laterally opposed side edges, wherein each of the prefastened disposible absorbent articles further includes a multi-functional fastening system comprising:

a) a pair of primary fasteners that are respectively located on the opposed side edges in the back waist region and that are refastenably prefastened during manufacture to the outer surface in the front waist region of the disposable absorbent article to define a waist perimeter dimension and to provide the prefastened disposable absorbent articles; and b) a secondary fastener that is located in the back waist region and that is configured to refastenably engage the outer surface in the front waist region to reduce the waist perimeter dimension and conform the waist regions to the wearer's body after the prefastened disposable absorbent article is pulled on over a wearer's hips.

2. The package of prefastened absorbent articles of claim 1 wherein the secondary fastener includes an extension member that defines an attached end that is secured to the absorbent article and a free end that includes a hook fastener that is configured to refastenably engage the outer surface in the front waist region of the absorbent article to conform the waist regions to the wearer's body.

3. The package of prefastened absorbent articles of claim 2 wherein the attached end of the extension member is located inward from the primary fasteners towards a longitudinal centerline of the absorbent article and the hook fastener and the free end of the extension member are configured to extend over at least one of the primary fasteners to refastenably engage the outer surface in the front waist region of the absorbent article to conform the waist regions to the wearer's body.

4. A prefastened disposable absorbent article comprising an absorbent, an interior surface configured to face a wearer's body in use, an outer surface opposite the interior surface, a front waist region, a back waist region, a crotch region which extends between and connects the waist regions and a pair of laterally opposed side edges, wherein the absorbent article further includes a multi-functional fastening system comprising:

a) a pair of primary fasteners that are respectively attached to and located on the opposed side edges of the back waist region and that are refastenably engaged during manufacture to the outer surface of the front waist region thereby defining a waist perimeter dimension; and b) a waist size adjustment means located in the back waist region and configured to refastenably engage the outer surface of the absorbent article in the front waist region for reducing the waist perimeter dimension of the absorbent article without releasing the primary fasteners in use to conform the waist regions to a wearer's body.

5. The prefastened absorbent article of claim 4 wherein the waist size adjustment means includes a secondary fastener which is located in the back waist region and which is configured to refastenably engage the outer surface in the front waist region.

6. The prefastened absorbent article of claim 4 wherein the waist size adjustment means includes:

a) a belt segment that is located in the back waist region wherein the belt segment defines an attached portion that is secured to the back waist region and laterally opposed end portions; and b) a pair of secondary fasteners that are respectively located on the opposed end portions of the belt segment and that are configured to refastenably engage the outer surface in the front waist region in use to conform the back waist region and the front waist region to the wearer's body.

7. A prefastened disposable absorbent article comprising an absorbent, an interior surface configured to face a wearer's body in use, an outer surface opposite the interior surface, a front waist region, a back waist region, a crotch region which extends between and connects the waist regions and a pair of laterally opposed side edges wherein the prefastened absorbent article further includes a multi-functional fastening system comprising:

a) a pair of primary fasteners that are respectively located on the opposed side edges in the back waist region and that are refastenably prefastened to the outer surface in the front waist region of the disposable absorbent article to refastenably engage the front waist region to the back waist region during manufacture to define a waist perimeter dimension and to provide the prefastened disposable absorbent article; and b) a secondary fastener that is located in the back waist region and that is configured to refastenably engage the outer surface of the absorbent article in the front waist region to reduce the waist perimeter dimension and conform the waist regions to the wearer's body after the prefastened disposable absorbent article is pulled on over a wearer's hips.

8. The absorbent article of claim 7 wherein the primary fasteners are hook fasteners.

9. The absorbent article of claim 8 wherein the secondary fastener is also a hook fastener.

10. The absorbent article of claim 7 wherein the multi-functional fastening system further includes an attachment panel that is located on the outer surface in the front waist region and wherein the primary fasteners are configured to refastenably engage the attachment panel.

11. The absorbent article of claim 7 wherein the multi-functional fastening system includes another secondary fastener, the pair of the secondary fasteners are respectively located on the opposed side edges of the absorbent article in the back waist region, wherein each of the secondary fasteners is also configured to refastenably engage the outer surface in the front waist region in use to conform the waist regions to the wearer's body.

12. The absorbent article of claim 7 wherein the secondary fastener includes an extension member that defines an attached end that is secured to the absorbent article and a free end that includes a hook fastener that is configured to refastenably engage the outer surface in the front waist region of the absorbent article in use to conform the waist regions to the wearer's body.

13. The absorbent article of claim 12 wherein the attached end of the extension member is located inward toward a longitudinal centerline of the absorbent article from the primary fasteners and the hook fastener and the free end of the extension member are configured to extend over at least one of the primary fasteners to refastenably engage the outer surface in the front waist region of the absorbent article to conform the waist regions to the wearer's body.

14. A prefastened disposable absorbent article comprising an absorbent, an interior surface configured to face a wearer's body in use, an outer surface opposite the interior surface, a front waist region, a back waist region, a crotch region which extends between and connects the waist regions and a pair of laterally opposed side edges wherein the prefastened absorbent article further includes a multi-functional fastening system comprising:

a) a pair of primary fasteners that are respectively located on the opposed side edges in the front waist region and that are refastenably prefastened to the outer surface in the back waist region of the disposable absorbent article to refastenably engage the back waist region to the front waist region during manufacture to define a waist perimeter dimension and to provide the prefastened disposable absorbent article; and b) a secondary fastener that is located in the front waist region and that is configured to refastenably engage the outer surface of the absorbent article in the back waist region to reduce the waist perimeter dimension and conform the waist regions to the wearer's body after the prefastened disposable absorbent article is pulled on over a wearer's hips.

\* \* \* \* \*